(12) United States Patent
Lord (10) Patent No.: US 11,081,239 B2
(45) Date of Patent: Aug. 3, 2021

(54) SYSTEM AND METHOD FOR CREATING COMPUTER INTERPRETABLE GUIDELINES USING A KNOWLEDGE ACQUISITION AND MANAGEMENT TOOL

(71) Applicant: KONINKLIJKE PHILIPS N.V., Eindhoven (NL)

(72) Inventor: William Palmer Lord, Fishkill, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 807 days.

(21) Appl. No.: 14/365,184

(22) PCT Filed: Dec. 11, 2012

(86) PCT No.: PCT/IB2012/057186
§ 371 (c)(1),
(2) Date: Jun. 13, 2014

(87) PCT Pub. No.: WO2013/088344
PCT Pub. Date: Jun. 20, 2013

(65) Prior Publication Data
US 2014/0379367 A1    Dec. 25, 2014

Related U.S. Application Data

(60) Provisional application No. 61/569,914, filed on Dec. 13, 2011.

(51) Int. Cl.
*G16H 70/20* (2018.01)
*G06N 5/02* (2006.01)
(Continued)

(52) U.S. Cl.
CPC ............. *G16H 70/20* (2018.01); *G06N 5/022* (2013.01); *G16H 10/20* (2018.01); *G16H 40/63* (2018.01); *G16H 50/20* (2018.01)

(58) Field of Classification Search
CPC ...... G06Q 50/22; G06Q 50/24; G06F 19/322; G06F 19/323–327; G06F 19/30;
(Continued)

(56) References Cited

U.S. PATENT DOCUMENTS 4,646,250 A * 2/1987 Childress .............. G06F 17/243
715/255
5,574,828 A * 11/1996 Hayward ............... G16H 15/00
706/45
(Continued)

FOREIGN PATENT DOCUMENTS

JP   2007097744 A   4/2007

OTHER PUBLICATIONS

Kosara et al., Tools for Acquiring Clinical Guidelines in Asbru, Integrated Design and Process Technology, IDPT-2002, Jun. 2002, 6 pages.*

(Continued)

*Primary Examiner* — Jason S Tiedeman (57) ABSTRACT

Described herein are systems and methods for transforming clinical guideline documents into computer interpretable guidelines ("CIGs"). One embodiment refers to a method comprising prompting a user, via a graphical user interface ("GUI"), for a plurality of clinical guideline entry steps, receiving, via the GUI, clinical guideline data, prompting the user, via the GUI, for a plurality of formal expression entry steps related to the clinical guideline data, receiving, via the GUI, a formal representation of the clinical guideline data and mapping the formal representation of the clinical data to a CIG.

13 Claims, 8 Drawing Sheets

(51) Int. Cl.
*G16H 10/20* (2018.01)
*G16H 40/63* (2018.01)
*G16H 50/20* (2018.01)

(58) Field of Classification Search
CPC ....... G06F 19/325; G06F 19/34; G16H 10/00; G16H 10/60; G16H 15/00; G16H 20/00; G16H 50/00; G16H 50/20; G16H 50/70
USPC .......................................................... 705/2, 3
See application file for complete search history.

(56) References Cited

U.S. PATENT DOCUMENTS

| | | | | |
|---|---|---|---|---|
| 8,439,835 | B1* | 5/2013 | McKinley | A61B 5/0205 600/301 |
| 9,165,116 | B2 | 10/2015 | Amies et al. | |
| 9,424,398 | B1* | 8/2016 | McLeod | G16H 10/40 |
| 2004/0216039 | A1* | 10/2004 | Lane | G06F 40/166 715/229 |
| 2004/0261063 | A1* | 12/2004 | Wang | G16H 70/20 717/136 |
| 2005/0108049 | A1* | 5/2005 | Ram | G06F 19/3481 705/2 |
| 2005/0119914 | A1* | 6/2005 | Batch | A61B 5/411 705/2 |
| 2005/0144482 | A1* | 6/2005 | Anuszewski | H04L 63/083 726/4 |
| 2006/0026205 | A1* | 2/2006 | Butterfield | G16H 20/10 |
| 2006/0111933 | A1* | 5/2006 | Wheeler | G06Q 10/06375 705/2 |
| 2006/0143043 | A1* | 6/2006 | McCallie, Jr. | G06Q 10/10 705/2 |
| 2007/0005394 | A1* | 1/2007 | Bleyendaal | G06Q 30/08 705/2 |
| 2007/0067182 | A1* | 3/2007 | Harp | G16H 10/60 705/2 |
| 2007/0078497 | A1* | 4/2007 | Vandanacker | A61N 1/37211 607/59 |
| 2007/0112782 | A1* | 5/2007 | Lobach | G06Q 10/00 |
| 2007/0175980 | A1* | 8/2007 | Alsafadi | G16H 70/20 235/380 |
| 2007/0250460 | A1* | 10/2007 | Armstrong | G06N 5/025 706/11 |
| 2007/0255712 | A1* | 11/2007 | Mahoney | G06F 16/182 |
| 2008/0097791 | A1* | 4/2008 | Alsafadi | G16H 70/20 705/3 |
| 2010/0211402 | A1* | 8/2010 | Eggena | G16H 40/20 705/2 |
| 2011/0276343 | A1* | 11/2011 | Lagor | G16H 50/20 705/2 |
| 2011/0301982 | A1* | 12/2011 | Green, Jr. | G06Q 10/06 705/3 |
| 2012/0310694 | A1* | 12/2012 | Van Zon | G16H 70/20 705/7.15 |
| 2013/0197938 | A1* | 8/2013 | Bayouk | G16H 10/60 705/3 |
| 2013/0275161 | A1* | 10/2013 | Dutta | G16H 70/20 705/3 |

OTHER PUBLICATIONS de Clercq et al., Approaches for creating computer-interpretable guidelines that facilitate decision support, Artificial Intelligence in Medicine (2004) 31, 28 pages.*

Shahar et al., A framework for a distributed, hybrid, multiple-ontology clinical-guideline library, and automated guideline-support tools, Journal of Biomedical Informatics 37 (2004) 325-344 (Year: 2004).*

Declercq, P.A. et al. "Approaches for creating computer-interpretable guidelines that facilitate decision support". Artificial Intelligence in Medicine May 2004;31(1), 1-27.

Correndo, Gianluca. "Using Contextualization techniques for enhaving clinical guidelines dessemination to heterogeneous hospital Information systems". Ph.D. Thesis. Universita' Degli Studi Di Torino.

Shahar, Y. et al., "A framework for a distributed, hybrid, multiple-ontology clinical-guideline library, and automated guideline-support tools", Journal of Biomedical Informatics 37 (2004) 325-344.

Clercq, P.A. et al., "Approaches for creating computer-interpretable guidelines that facilitate decision support", Artificial Intelligence in Medicine (2004) 31, 1-27.

Peleg, M., et al., "The InterMed Approach to Sharable Computer-interpretable Guidelines: A Review", Journal of the American medical Informatics Association, vol. 11, No, 1.

Skonetzki, S. et al., "HELEN, a modular framework for representing and implementing clinical practice guidelines". Department of Medical Informatics, Heidelberg University Medical Center, Germany, 2004, pp. 413-426.

Shankar, R., et al., "Use of Protege-2000 to Encode Clinical Guidelines", AMIA Annual Symposium, Jan. 1, 2002.

Latoszek Berendsen, A. et al., "From Clinical Practice Guidelines to Computer Interpretable Guidelines", Methods of Information in Medicine, vol. 49, Nr.

Shankar, R. et al., "Use of Protege-2000 to Encode Clinical Guidelines". AMIA Annual Symposium, Jan. 1, 2002. The entire document.

Skonetzki, S., et al., "Helen, a modular framework for representing and implementing clinical practice guidelines", Methods of Information in Medi, Jan. 1, 2004 Schattauer GmbH, DE, vol. 43, Nr: 4, pp. 413-426.

Boxwala, A. "GLIF3: a representation format for sharable computer-interpretable clinical practice guidelines", Journal of Biomedical Informatics, Jun. 1, 2004.

Latoszek Berendsen, A. et al., "From Clinical Practice Guidelines to Computer interpretable Guidelines", Methods of Information in Medicine, vol. 49, Nr. 6, pp. 550-570.

Boxwala, A.A., "GLIF3: a representation format for sharable computer-interpretable clinical practice guidelines", Journal of Biomedical Informatics, pp. 147-161, 2004.

Latoszek-Berendsen et al., "From Clinical Practice Guidelines to Computer-interpretable Guidelines". Methods of Information in Medicine, vol. 49, Nr: 6, p. 550-570.

Ravi Shankar et al., "Use of Protege-2000 to Encode Clinical Guidelines". AMIA Annual Symposium, Jan. 1, 2002.

Skonetzki, S. et al., "HELEN, a modular framework for representing and implementing clinical practice guidelines". Methods of Information in Medi, Jan. 1, 2004 Schattauer GmbH, DE, vol. 43, Nr: 4, p. 413-426.

* cited by examiner

SYSTEM AND METHOD FOR CREATING COMPUTER INTERPRETABLE GUIDELINES USING A KNOWLEDGE ACQUISITION AND MANAGEMENT TOOL

This application is a national stage application under 35 U.S.C. § 371 of International Application No. PCT/IB2012/057186 filed on Dec. 11, 2012 and published in the English language on Jun. 20, 2013 as International Publication No. WO/2013/088344, which claims priority to U.S. Application No. 61/569,914 filed on Dec. 13, 2011, the entire disclosures of which are incorporated herein by reference.

Clinical guidelines refer to recommendations for the treatment and care of medical conditions. These guidelines consist of for example, decisions and decision criteria for diagnosis, management, and treatment of patients in specific areas of healthcare. Modern clinical guidelines identify, summarize and evaluate the highest quality evidence and most current data available about prevention, diagnosis, prognosis, therapy (e.g., dosage of medications), risk/benefit evaluations and cost-effectiveness. Accordingly, these clinical guidelines may define the most important questions related to clinical practice and identify the most possible decision options and their outcomes. Clinical guidelines are usually produced at both national and international levels by medical associations or governmental bodies.

Generally, the objectives of clinical guidelines are to standardize medical care, to raise quality of care, to reduce several kinds of risk to both the patient and the healthcare provider, and to achieve the best balance between cost and medical parameters such as effectiveness, specificity, sensitivity, etc. In addition, clinical guidelines may contain decision or computation algorithms that may be followed in order to integrate various decision points and respective courses of action with the clinical judgment and experience of practitioners. However, the computation algorithms currently used within these clinical guidelines increase the overall complexity of the decision making process.

Described herein are systems and methods for transforming clinical guideline documents into computer interpretable guidelines ("CIGs"). One embodiment refers to a method comprising prompting a user, via a graphical user interface ("GUI"), for a plurality of clinical guideline entry steps; receiving, via the GUI, clinical guideline data; prompting the user, via the GUI, for a plurality of formal expression entry steps related to the clinical guideline data; receiving, via the GUI, a formal representation of the clinical guideline data; and mapping the formal representation of the clinical data to a computer interpretable guideline ("CIG").

A further embodiment refers to a system comprising a graphical user interface ("GUI"); a knowledge acquisition and management ("KAM") prompting a user via the GUI for a plurality of clinical guideline entry steps, receiving clinical guideline data, further prompting the user via the GUI for a plurality of formal expression entry steps related to the clinical guideline data, and receiving a formal representation of the clinical guideline data; and a mapping module mapping the formal representation of the clinical data to a computer interpretable guideline ("CIG").

A further embodiment refers to a non-transitory computer readable storage medium including a set of instructions that are executable by a processor, the set of instructions being operable to prompt a user, via a graphical user interface ("GUI"), for a plurality of clinical guideline entry steps; receive, via the GUI, clinical guideline data from a user; prompt a user, via the GUI, for a plurality of formal expression entry steps related to the clinical guideline data; receive, via the GUI, a formal representation of the clinical guideline data; and map the formal representation of the clinical data to a computer interpretable guideline ("CIG").

The exemplary embodiments may be further understood with reference to the following description of exemplary embodiments and the related appended drawings, wherein like elements are provided with the same reference numerals. The exemplary embodiments are related to systems and methods for transforming clinical guideline documents into computer interpretable guidelines ("CIGs").

As noted above, clinical guidelines ("GLs") may be used to document recommendations for the treatment and care of medical conditions. Typically, GLs consist of decisions and decision criteria for diagnosis, management, and treatment of patients with these medical needs. The medical needs can be for specific diseases and conditions, multiple diseases, triage, diagnosis, patient populations, well care, etc. The CIGs may be considered the computer interpretable representations of the clinical knowledge contained in these clinical GLs.

Recent studies have shown that adhering to the recommendations of these clinical GLs reduces costs and improves outcomes. As a result, guideline adherence is increasingly tied to performance measures and reimbursements. This creates an opportunity for healthcare solutions, in particular clinical decision support ("CDS") systems and applications, to use CIG technologies to support this trend.

According to the exemplary systems and methods described herein, generating CIGs may require both clinical knowledge of medical treatment as well as formal representation (e.g., computer-based) knowledge. The exemplary embodiments may utilize a knowledge acquisition and management ("KAM") tool for the creation and maintenance of the CIGs in a collaborative manner. It should be noted that while the embodiments described throughout this disclosure may be directed towards clinical guidelines and treatments, these systems and methods may be applicable to any guideline, protocol, workflow, and/or pathway-based embodiment outside the medical field.

Figure 1:
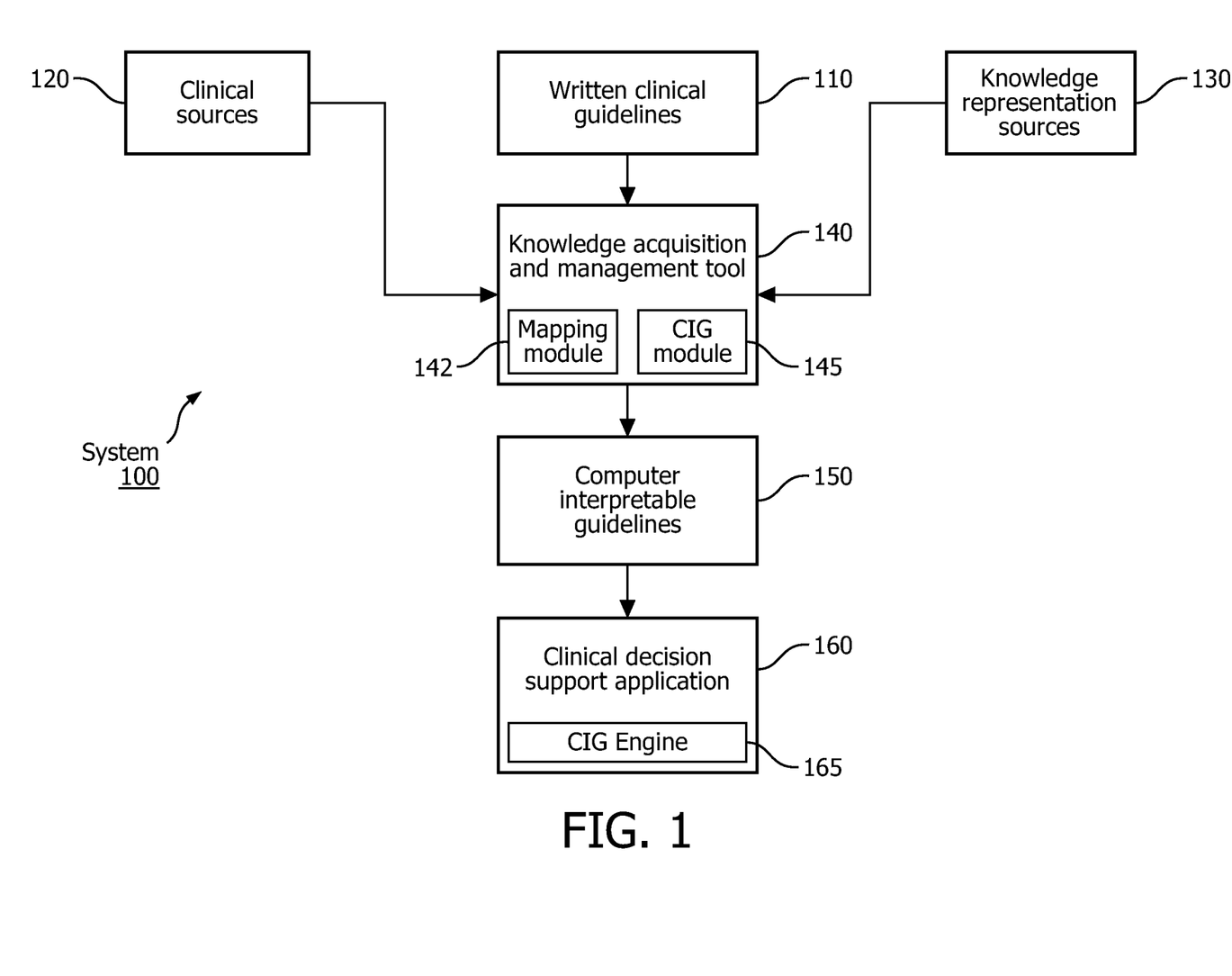
FIG. 1 shows an exemplary flowchart for transforming a clinical guideline into a computer interpretable guideline ("CIG") using a knowledge acquisition and management ("KAM") tool according to an exemplary embodiment described herein.

FIG. 1 shows an exemplary system 100 for transforming a written clinical guideline ("GL") 110 into a computer interpretable guideline ("CIG") 150. The architecture of the system 100 includes, for example, building blocks (e.g., components) and interfaces among these blocks for creating configurable, extensible, and reusable CIGs from various clinical GLs. While the term CIG will be used throughout this disclosure, alternative terms may include "executable clinical guidelines" and "automated practice guidelines." The system 100 architecture includes computer-executable components which include computer-readable instructions or code stored on a computer-readable medium and executable by a processor for performing certain functions as described in greater detail below The system 100 utilizes a knowledge acquisition and management ("KAM") tool 140 for transforming the written clinical GL 110 into the computer-readable CIG 150. Specifically, the KAM tool 140 includes a mapping module 142 and at least one CIG model 145. The mapping module 142 maps formal representations of clinical guideline data into the exemplary CIG 150. The CIG model 145 defines a formal manner for representing the knowledge found within the clinical GL 110. Therefore, the CIG model 145 designates the manner in which clinical concepts, relevant control concepts, and their relationships can be represented within the CIG 150.

Once the written clinical GL 110 is provided to the KAM tool 140, input may be received at the KAM tool 140 from clinical sources 120 (e.g., clinical experts) and formal representation sources 130 (e.g., knowledge engineers). Specifically, the knowledge engineers 130 may use the KAM tool 140 to author the CIG 150 based on the underlying CIG model 145. The CIG 150 generated by the knowledge engineers 130 includes, for example, guideline representations, application-specific representations, and site-specific representations. As will be described in greater detail below, the collaborative authoring by the clinical experts 120 and the computer-based formal representation sources 130 allow for the KAM tool 140 to generate the reusable CIG 150 from the clinical GL 110.

According to the exemplary system 100, a CIG engine 165 is provided to run the instructions contained in the CIG 150. In other words, the CIG engine 165 interprets and executes the exemplary CIG 150 according to the formal representations provided by the knowledge engineers 130. The CIG engine 165 may be utilized by, or may be a part of, a Clinical Decision Support ("CDS") application 160. A CDS application or system is an interactive decision support system using computer software to assist physicians and other health professionals with decision making tasks, such as determining diagnosis of patient data. It should be noted that while the CIG engine 165 is described as a component within the CDS application 160, any of the components within the system 100 may either be stand-alone components or integrated with one or more other components.

The recommendations provided by the CIG 150 may generally be customized both to the specific CDS application 160 that employs the CIG 150 and to the site wherein the CIG 150 will be used. In order to maximize reusability, each of the components within the exemplary system 100 may be entirely extensible. For example, the KAM tool 140 and the CIG model 145 may provide a fixed, reusable core that may be extended to support many specific CDS applications.

As indicated above, the KAM tool 140 and any of its various components (e.g., the CIG modeling component 145, etc.) may be implemented as software instructions executable by a processor. Furthermore, the KAM tool 140 may include a separate processor and a non-transitory computer readable storage medium, such as a memory. Accordingly, the memory may include the set of software instructions that are executable by the processor. It should be noted that, each of the components of the KAM tool 140 may also include an individual processor, memory and corresponding instructions, thereby creating a multi-processor architecture for the KAM tool 140.

The exemplary system 100 including the KAM tool 140 may ease users through the complexity of creating the CIG 150. The system 100 may use context specific tools to provide users with the best tool for specific tasks. Furthermore, the system 100 may provide user-specific tools based on an anticipated background or experience level of different users working in a collaborative manner. It should be noted that the term "user" may refer to any operator of the systems and methods described herein, including, but not limited, to application/knowledge engineers, IT personnel, clinical specialists, physicians, nurses, practitioners, etc.

Figure 2:
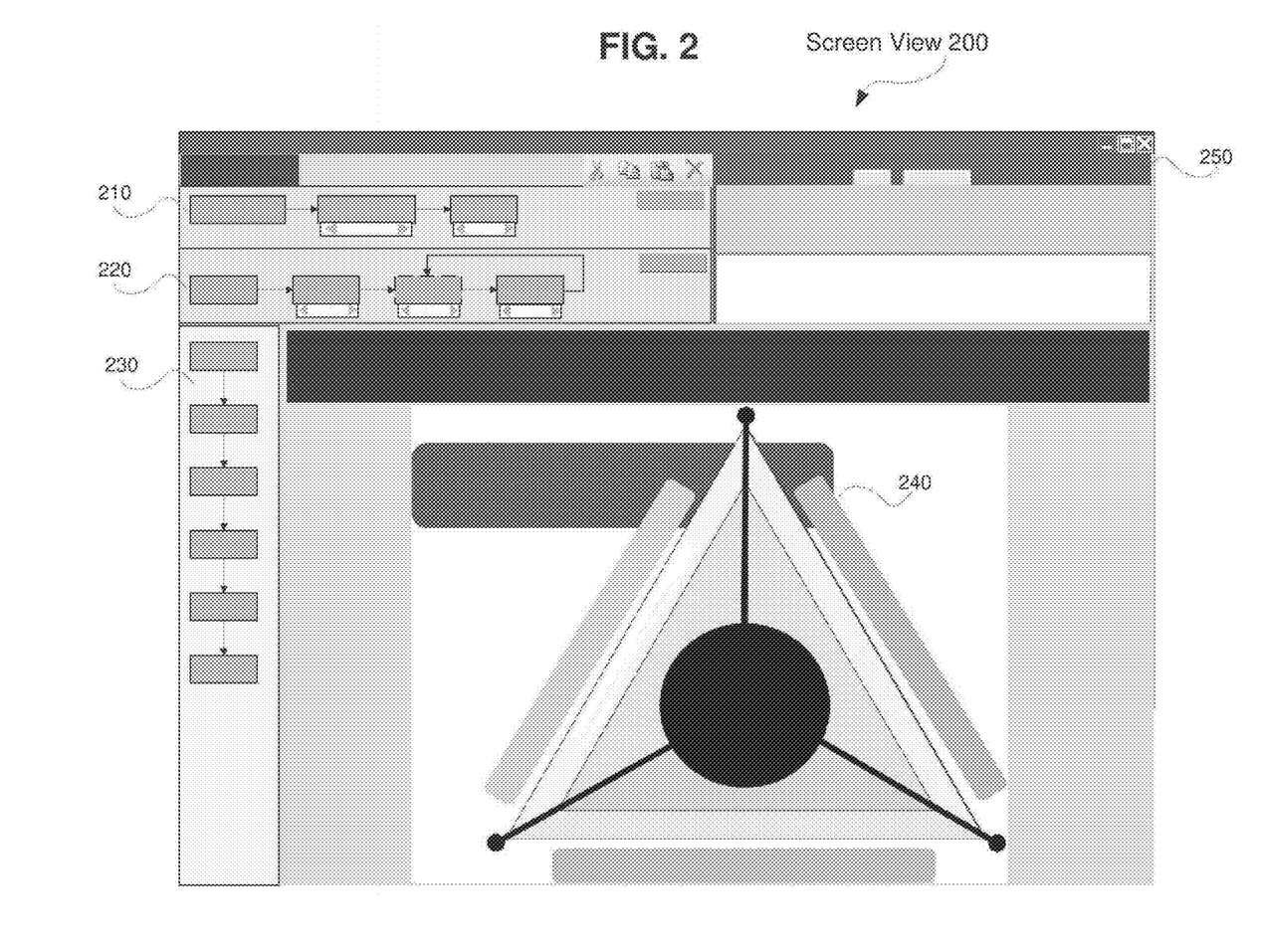
FIG. 2 shows an exemplary screen view of a start-up page for the KAM tool according to an exemplary embodiment described herein.

FIG. 2 shows an exemplary screen view 200 of a start-up screen, or log-in page for the KAM tool 140 according to an exemplary embodiment described herein. It should be noted that exemplary screen view 200, as well as each of the other screen views herein, will be discussed with reference to KAM tool 140 and related components of the system 100 illustrated in FIG. 1.

The exemplary start-up screen view 200 allows a user to open and modify existing content (e.g., the CIG 150) or create new content. The start-up screen view 200 serves as a graphical user interface ("GUI") representing progressive flow diagrams of the CIG creation process. Specifically, these flow diagrams provide status information and updates during the transformation of the clinical GL 110 to the CIG 150. Furthermore, the exemplary GUI and the KAM tool 140 may be a web-based portal accessible to any number of users on a network having authorized log-in credentials.

The exemplary flow diagrams of the screen view 200 include an overview flow diagram 210, a content-specific flow diagram 220, and a step progress flow diagram 230. Each of these flow diagrams 210-230 indicates various phases the user will navigate as the CIG 150 is authored. This view 200 assists the user in navigating through the use of the KAM tool 140 by providing visual cues (e.g., a "you are here" progress-tracking feature). For instance, the screen view 200 may highlight or "bold" a step box within one or more flow diagrams to indicate the current stage to the user. Furthermore, the screen view 200 may use color-coded boxes in the flow diagrams to indicate completed, partially completed, and incomplete steps within the process.

An extensible guideline model 240 illustrates the overview flow diagram 210 that refers to the broadest, high-level stages for the creation of the CIG 150. A first stage of the overview flow diagram 210 is directed toward the collection of general clinical content, such as an informal description of the CIG 150 from the clinical expert 120 and a formal description of the CIG 150 from the knowledge engineers 130. Within this general clinical content stage of the flow diagram 210, the step progress flow diagram 230 includes information such as name, organization, author(s), version number, description, and clinical goal of the CIG 150.

A second stage of the overview flow diagram 210 is directed toward the application specific content, such as clinical application properties from the clinical expert 120 and formal CIG application properties from the knowledge engineers 130. As will be described in greater detail below, the application specific properties may include information related to various medical devices and specific CDS applications. When the user has selected or highlighted this stage, the step progress flow diagram 230 illustrates steps associated with this stage.

A third stage of the overview flow diagram 210 is directed toward the site specific content, such as site specific customization from the clinical expert 120 and virtual references to actual site content from the knowledge engineers 130. As will be described in greater detail below, the site-specific content may include site protocols (e.g., hospital policies and regulations), information sources (e.g., hospital records and lab systems), etc.

It should be noted that the KAM tool 140 may also include an instant messaging system 250. The messaging system 250 may be available to the user through the CIG creation process for communication between collaborative parties. For instance, a clinical expert may transmit information via an instant message to a knowledge engineer while the KAM tool 140 is in use, a knowledge engineer may query a clinical expert for further clarification on a medical step, etc.

Figure 3:
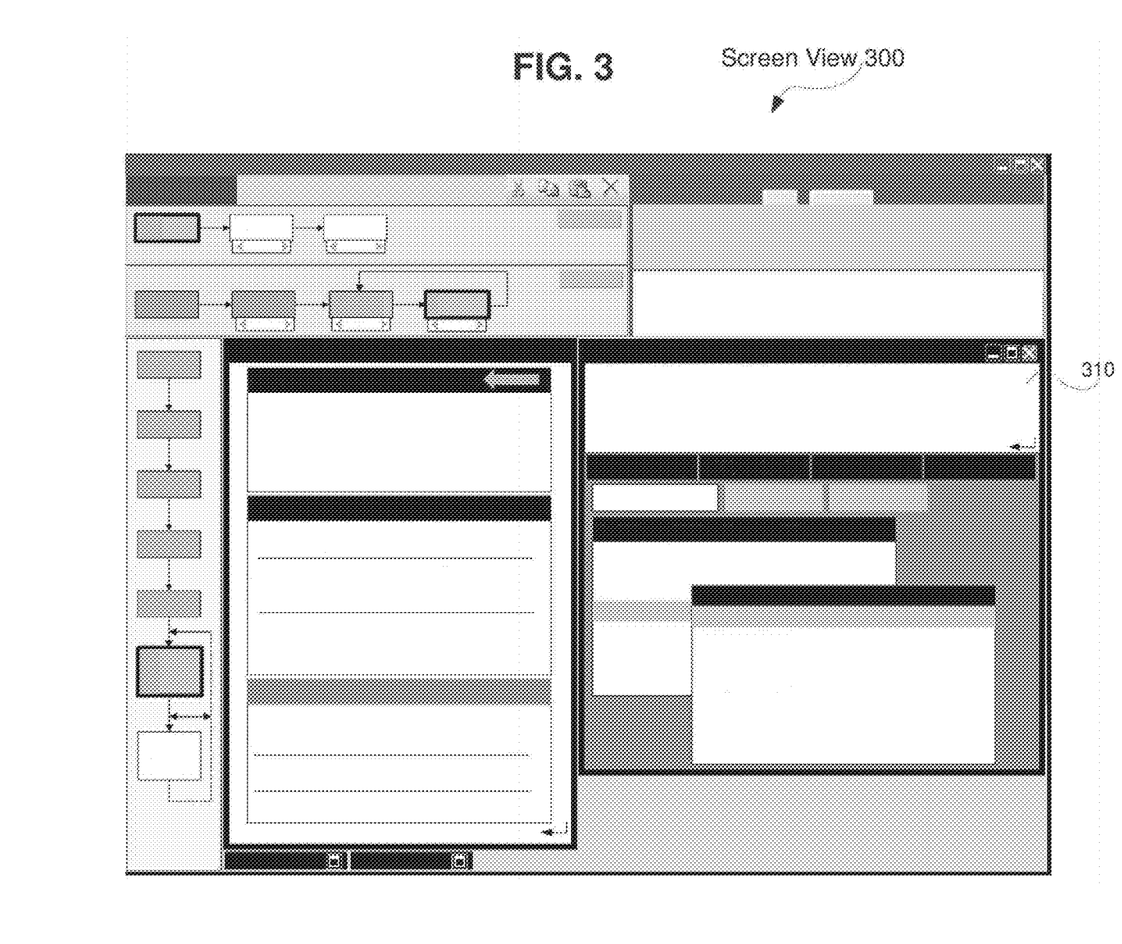
FIG. 3 shows an exemplary screen view of an expression wizard for expression creation within CIGs of the KAM tool according to an exemplary embodiment described herein.

FIG. 3 shows an exemplary screen view 300 of an expression wizard window 310 for expression creation within the CIG 150 of the KAM tool 140 according to an exemplary embodiment described herein. The expression wizard window 310 is a formal expression representing the informal text description provided by the clinical experts 120. In other words, once the clinical experts 120 have provided an information description of a guideline step, the knowledge engineer 130 may utilize the expression wizard window 310 to generate a formal expression of the clinical step.

For instance, the example depicted in screen view 300 relates to a triggering process (e.g., step, condition, recommendation) for detecting a risk of coronary heart disease ("CHD"). In this example, the clinical expert 120 indicates that if a CHD risk exam was last performed more than 3 to 5 years ago, then the guideline recommends for the physician to evaluate the presence and status of major risk factors. Accordingly, the knowledge engineer 130 may examine the informal description of the step/condition/recommendation and use the expression wizard window 310 to create a formal expression for each of the step, entry condition and recommended action information.

It should be noted that the expression wizard window 310 may incorporate context-sensitive menus (e.g., pull-down menus, drop-down lists, checkboxes, etc.) for building the formal expressions. The use of context-sensitive menus may ensure that only syntactically and semantically correct options are available to the formal expression author. For instance, the expression wizard window 310 may prohibit a conditional entry (e.g., "yes" or "no") in a field that requires an entry in a date format (e.g., 01/01/2001). The context-sensitive menus in the expression wizard 310 used to build these syntactically and semantically correct expressions are derived by the KAM tool 140 from the CIG Model 145.

Figure 4:
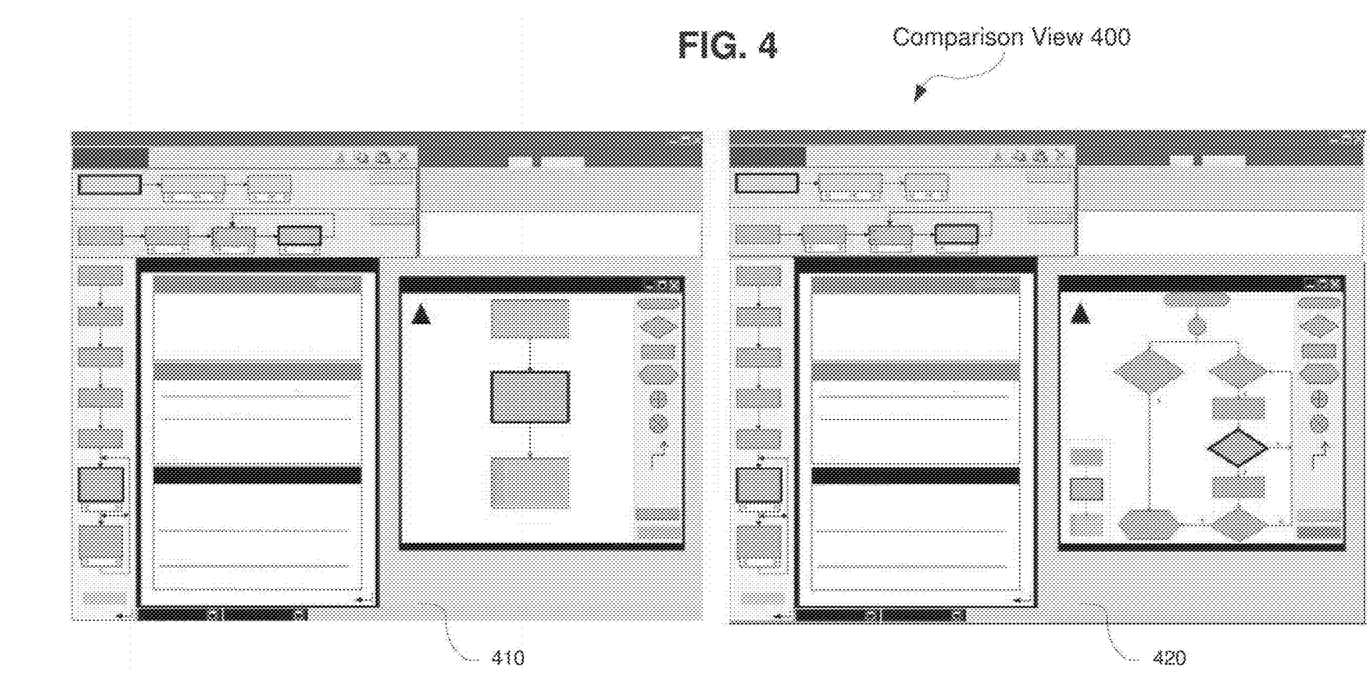
FIG. 4 shows a comparison between two exemplary screen views of both a clinical process view and formal process view displayed by the KAM tool according to an exemplary embodiment described herein.

FIG. 4 shows a comparison 400 between two exemplary screen views of both a clinical process view 410 and formal process view 420 displayed by the KAM tool 140 according to an exemplary embodiment described herein. As described above, the KAM tool 140 is a collaborative tool allowing the clinical experts 120 to work in conjunction with the knowledge engineers 130. The two views 410, 420 illustrate how these various types of user-authors may work with the KAM tool 140. Accordingly, each user may utilize their specific display for navigating the KAM tool 140 during the creation of the CIG 150.

The clinical process view 410 of FIG. 4 depicts a more simple, high-level view of a specific clinical process as authored by the clinical expert 120. In other words, the clinical expert 120 generates this high-level view upon specifying key clinical elements referenced by an exemplary GL. The formal process view 420 depicts a graphical representation as it may be built up by the knowledge engineer 130 who is responsible for authoring the complete formal specification of the CIG. Specifically, the knowledge engineer 130 maps each of the key elements identified in the clinical process view 410 to elements within the formal representation (e.g., CIG model 145) of the formal process view 420. As described above, the CIG model 145 of formal process view 420 may be interpreted by a computer (e.g., the CIG engine 165 of the CDS application 160).

Figure 5:
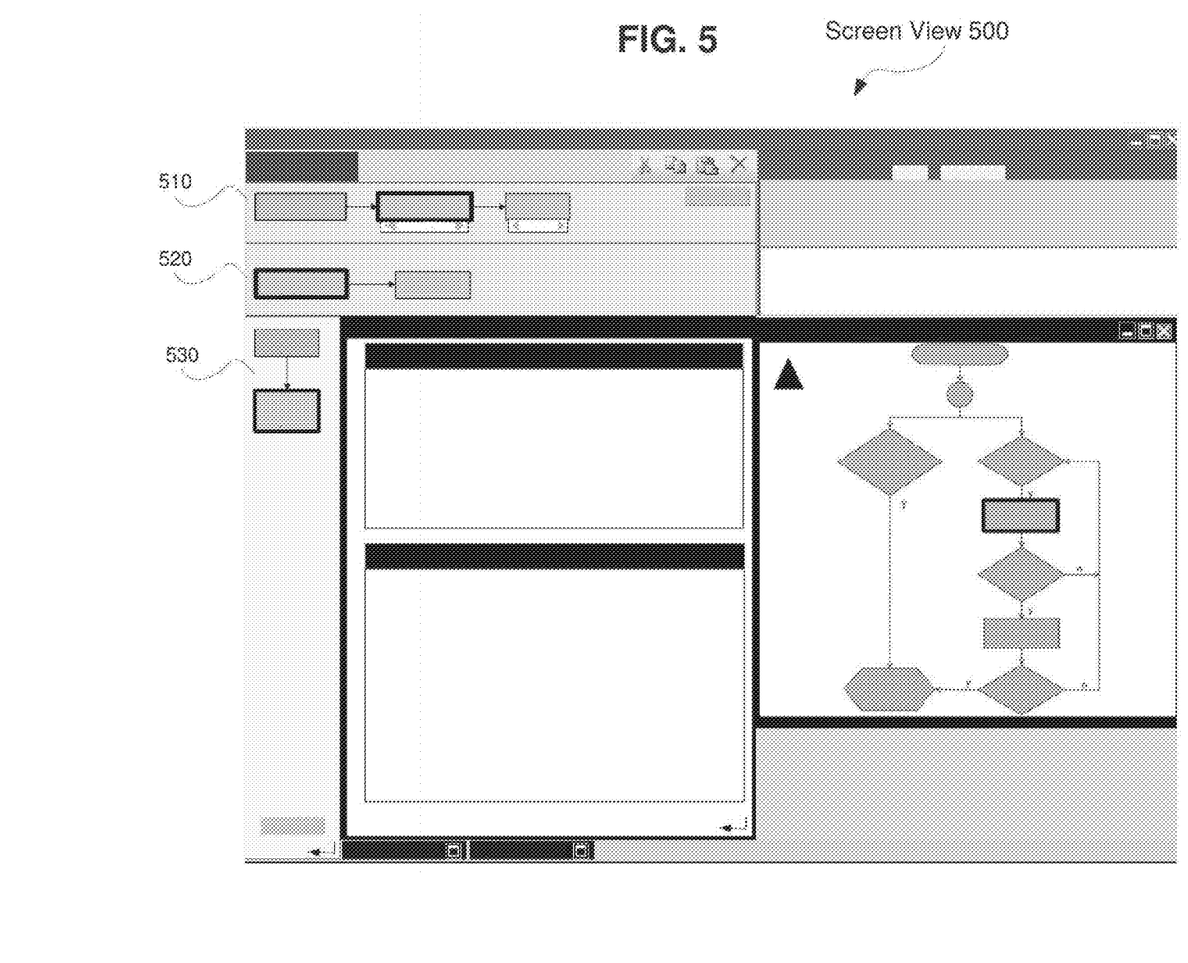
FIG. 5 shows an exemplary screen view for adding node specific properties to a CIG using the KAM tool according to an exemplary embodiment described herein.

FIG. 5 shows an exemplary screen view 500 for adding node specific, or context specific, properties to the CIG 150 using the KAM tool 140 according to an exemplary embodiment described herein. According to the exemplary KAM tool 140 and CIG 150, the nodes are defined as each of the steps or decision points throughout the clinical GL 110. Many of the properties to be associated with these nodes may be known in advance. Therefore, the KAM tool 140 lists all of the known properties and allows for the user to edit each property using various property appropriate tools.

Similar to the exemplary flow diagrams of the screen view 200 above, the screen view 500 includes an overview flow diagram 510, an application-specific flow diagram 520, and a step progress flow diagram 530. As noted by the bolded highlight, the current stage along the overview flow diagram 510 is the "Application Specific Content" stage. Within this stage, the application-specific flow diagram 520 indicates that the user may enter CDS application specific properties. Furthermore, the step progress flow diagram 530 indicates that the user may enter either global properties or node specific properties within the exemplary CDS application 160. Specifically, the screen view 500 illustrates how a user may use extensible markup language ("XML") to assign additional properties to the highlighted node (e.g., within the "Group/node specific properties" window).

Accordingly, the KAM tool 140 has the ability to continuously add and modify any number of node specific properties. These properties may relate to certain CDS applications and/or specific sites used by CIGs, groups within CIGs, and nodes within CIGs and groups. Therefore, the KAM tool 140 provides an extensible guideline model that extends the knowledge of any CIG, and allows the author of the CIG to be aware of possible expansion to the current content of the CIG (e.g., if a certain hospital changes a policy regarding a guideline, a node within the corresponding CIG may be easily modified to account for the change).

Figure 6:
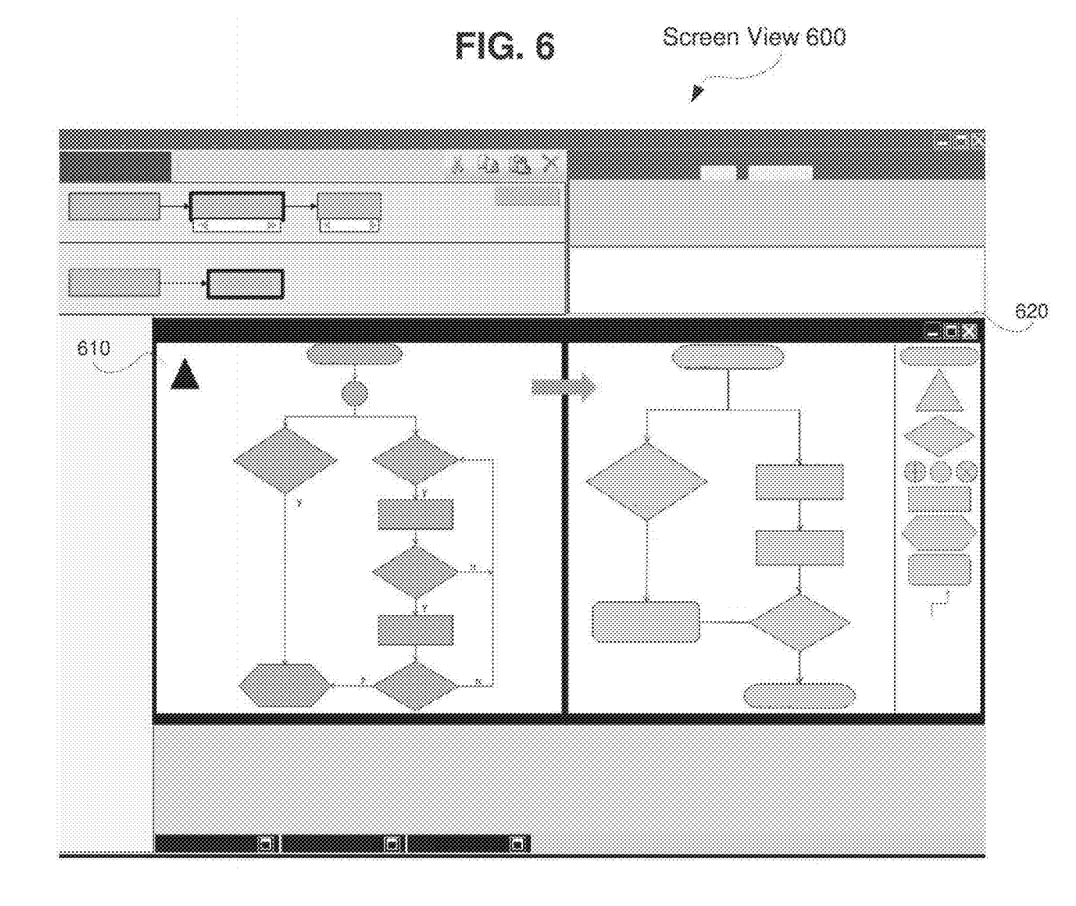
FIG. 6 shows an exemplary screen view of both an author's view of a CIG and an application-specific view of the CIG using the KAM tool according to an exemplary embodiment described herein.

FIG. 6 shows an exemplary screen view 600 of both an author's view 610 of the CIG 150 and an application-specific view 620 of the CIG 150 using the KAM tool 140 according to an exemplary embodiment described herein. As described above, the KAM tool 140 provides the ability to map a graphical representation for an overview of a clinical guideline. However, the graphical representations built up for authoring may not necessarily be the representation desired for a certain end-user CDS application. For CDS applications that want to create a customized view, the screen view 600 illustrates how the user may start with one of the graphical overviews used for authoring (e.g., author's view 610), and then edit the view to be specific to its customized application (e.g., application specific view 620).

According to one example, a user may want to edit the initial overview by combining two steps into one. When this is done, the combined step/node may be required to contain the properties of both originating nodes. In order to facilitate this process, the KAM tool 140, for instance may, logically insert an "or" step prior to the entry conditions of the original nodes for the combined nodes, and may logically insert an "and" step to the subsequent completeness conditions for the combined nodes. Therefore, the KAM tool 140 automates the process of merging multiple steps in a CIG while maintaining various properties of the underlying guideline.

Figure 7:
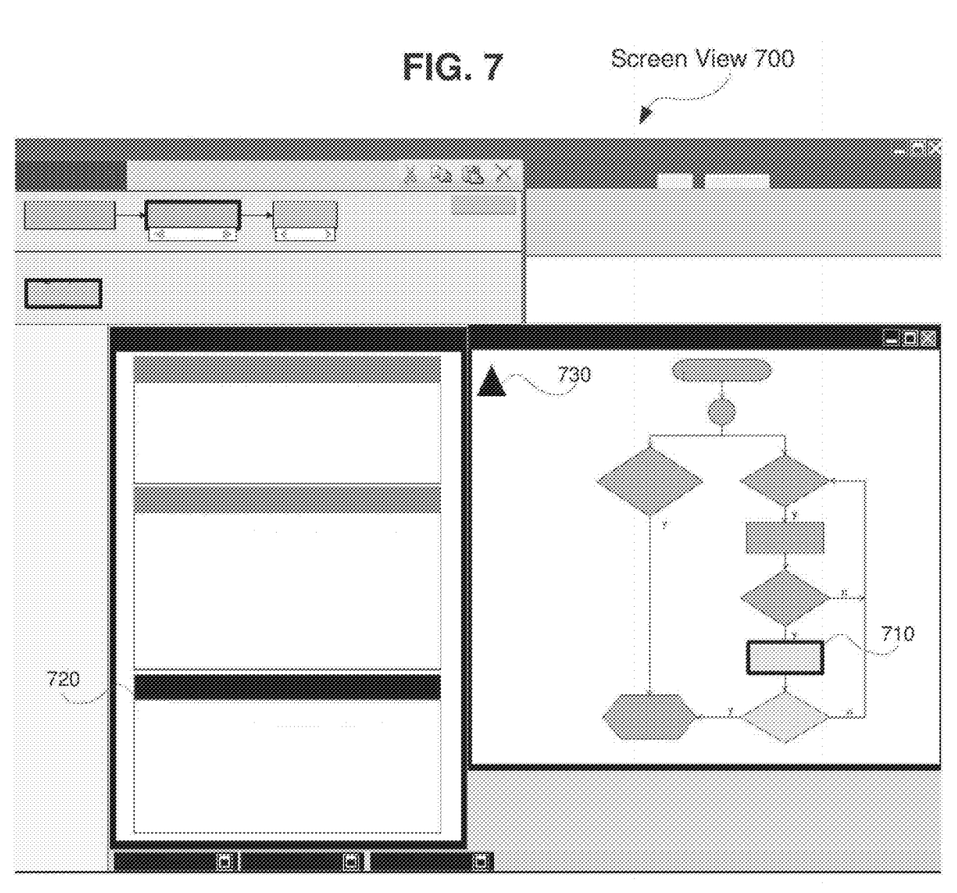
FIG. 7 shows an exemplary screen view for highlighting nodes that require further specification input using the KAM tool according to an exemplary embodiment described herein.

FIG. 7 shows an exemplary screen view 700 for highlighting nodes that require further specification input using the KAM tool 140 according to an exemplary embodiment described herein. At appropriate time in the authoring process, the KAM tool 140 detects incomplete and/or erroneous entries within the CIG 150. When one of these conditions occurs, the KAM tool 140 alerts the user by highlighting the specific node in the graphical representation of the CIG 150. The highlighting feature may be in the form of a designated color-coding, flashing, or any other device that calls attention to the node requiring further user intervention. Additionally, upon selecting the highlighted node by the user, the exact problem in question is indicated within the text entry window of the KAM tool 140. According to the example illustrated in the screen view 700, the node 710 is highlighted as reading "Calculate 10 yr risk" while Recommendation text entry window 720 is highlighted as reading "Recommend(CHD_10_Year_Risk).

Due to the fact that CIGs may typically be hierarchical, it is possible that a node in question is not visible on the graphical representation of the CIG. If this is the case, then the KAM tool 140 may highlight the parent node of the node in question, or the parent of the parent node. If the node and none of its ancestors are currently visible on the graphical representation, the KAM tool 140 may provide a navigation arrow 730 to direct the user to the node in question. In the case that a non-visible node is highlighted, the navigation arrow would also be highlighted to indicate that a non-visible node still needs attention. Specifically, the navigation arrow 730 is used to navigate the user back up the hierarchy of the CIG.

Figure 8:
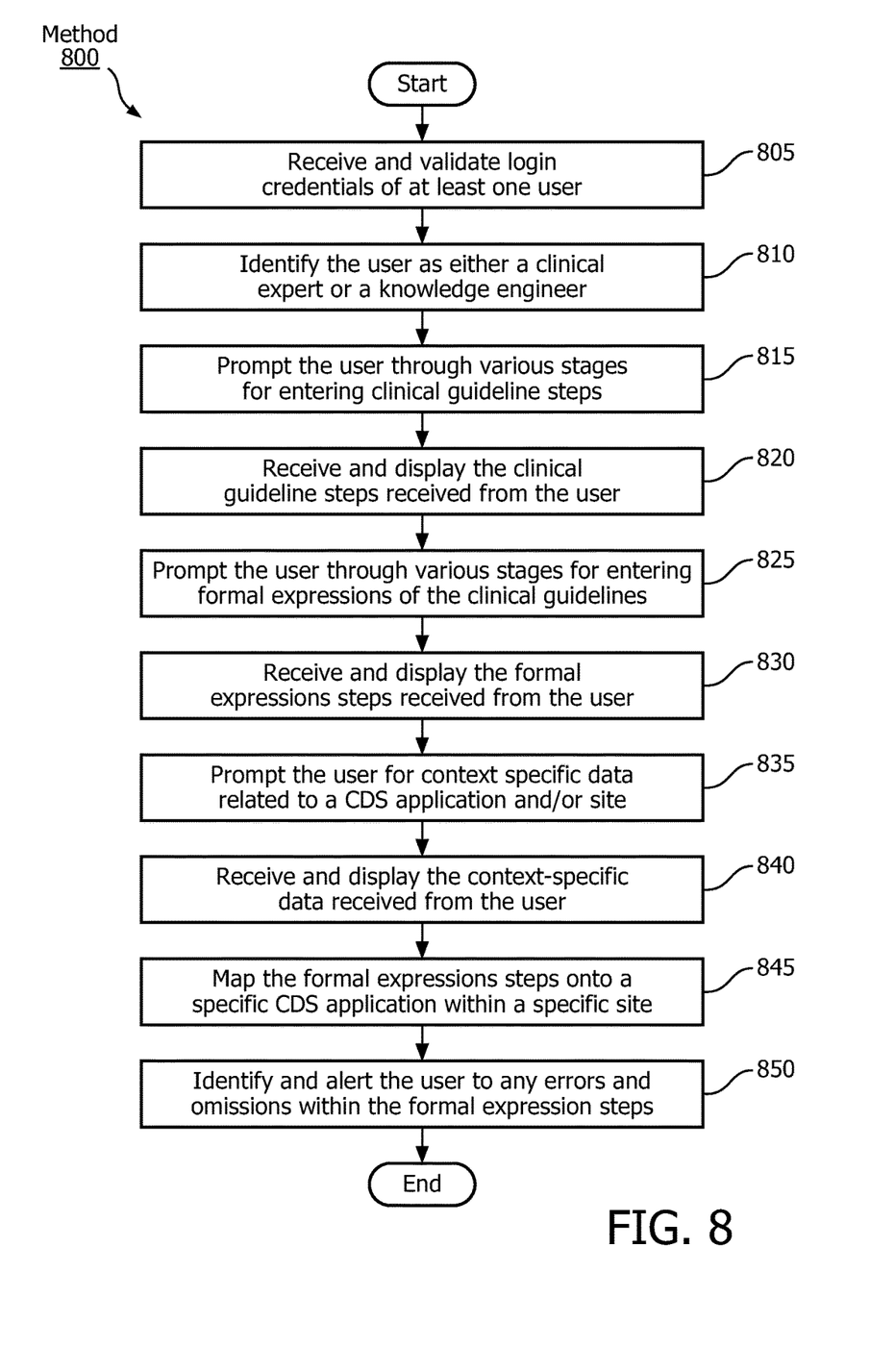
FIG. 8 shows an exemplary method for transforming a clinical guideline into a CIG using the KAM tool according to an exemplary embodiment described herein.

FIG. 8 shows an exemplary method 800 for transforming a clinical guideline into the CIG 150 using the KAM tool 140 according to an exemplary embodiment described herein. It should be noted that method 800 will be discussed with reference to KAM tool 140 and related components of the system 100 illustrated in FIG. 1.

As detailed above, the KAM tool 140 allows for users (e.g., clinical experts 120 and knowledge engineers 130) to transform clinical guideline documents into CIGs. According to one of the exemplary embodiments, the KAM tool 140 is a network-based software tool utilizing a communication service to allow users to read, create, augment, interpret, compare and correlate clinical guideline data as well as formal computer-based representations of the clinical data.

Beginning with step 805, the KAM tool 140 receives and validates log-in credentials of at least one user. As noted above, the KAM tool 140 may be a web-based portal accessible to users over a network (e.g., the Internet, a local intranet, etc.). Thus, the KAM tool 140 may use the log-in credentials to ensure system security and data integrity.

In step 810, the KAM tool 140 identifies the user as either a clinical expert or a knowledge engineer. As noted above, the KAM tool 140 may be accessible to both clinical experts 120 and knowledge representation experts 130. According to one embodiment, the KAM tool 140 identifies the user as one of these experts based on the user's log-in credentials. Therefore, the KAM tool 140 adjusts various setting to accommodate different types of user (e.g., informal clinical view and formal expression view). It should be noted that certain users may also be capable of switching between the various settings within the KAM tool 140.

In step 815, the KAM tool 140 prompts the user through various stages for entering clinical guideline steps. As noted above, the KAM tool 140 provides visual cues to the clinical expert 120 throughout the CIG generation process. These visual cues may be in the form of highlighted and/or bold boxes within various flow charts depicted by the KAM tool 140. As the user completes the authoring for each stage of the CIG generation process, the KAM tool 140 prompts the user as to the next stage of the process. Accordingly, the prompt provided by the KAM tool 140 may serve as a navigation tool to the user throughout the process.

In step 820, the KAM tool 140 receives and displays the clinical guideline steps received from the user. For instance, the clinical expert 120 may provide the informal clinical data based on a written guideline. As noted above, the informal clinical data may be in the form of step-by-step instructions directed toward medical personnel for adhering to the clinical guidelines. The informal clinical data may be entered by the user via the GUI of the KAM tool 140. As the instructions are entered by the user, the KAM tool 140 displays them in the appropriate text windows throughout each of the steps of the guideline.

In step 825, the KAM tool 140 prompts the user through various stages for entering formal expressions of the clinical guidelines. Similar to the step 815 above, the KAM tool 140 provides visual cues to the knowledge engineer 130 throughout the CIG generation process. These visual cues may be in the form of highlighted and/or bold boxes within various flow charts and may prompt the user as to each stage of the process.

In step 830, the KAM tool 140 receives and displays the formal expressions steps received from the user. For instance, the knowledge engineers 130 may provide the formal computer-based expressions for each of the guideline steps provided by the clinical expert 120. As noted above, the formal expressions may be in the form of computer readable instructions (e.g., XML language, etc.) interpretable by one or more CDS applications/systems. The formal expression data may be entered by the user via the GUI of the KAM tool 140.

In step 835, the KAM tool 140 prompts the user for context specific data related to a CDS application and/or site. As noted above, the KAM tool 140 advances the user throughout the CIG generation process via visual cues. One the user has entered general clinical content from the overview flow diagram 210, the KAM tool 140 prompts the user for application specific content as well as site specific content.

In step 840, the KAM tool 140 receives and displays the context-specific data received from the user. As noted above, the formal expressions provided by the knowledge engineer 130 are built up using context-sensitive windows. These windows may contain syntactically and semantically correct menus to ensure the proper data and data format is entered during the CIG generation process. Furthermore, the context specific data may customize the CIG towards a specific CDS application/system or a specific location. For instance, the steps of the formal expressions may be tailored to a certain device on which it will operate. Additionally, the steps of the formal expressions may also be tailored to be specific to a certain hospital in which it will be deployed.

In step 845, the KAM tool 140 maps the formal expressions steps onto a specific CDS application within a specific site. Based on the specific application content and site content provided by the knowledge engineer in step 840, the graphical representation of the exemplary CIG 150 is mapped by the mapping module 142 to the CDS application 160. As noted above, the recommendations provided by the CIG 150 are customizable to any specific CDS application or system and the site where the CIG 150 will be used. To maximize the reusability for each of the CIGs generated by the KAM tool 140, each of the components of the tool 140 are extensible to support any number of CDS applications as well as any changes or modifications to existing CDS applications. Thus, the KAM tool 140 is capable of extending the knowledge for each CIG in order to be adaptable to new CDS devices and changes in hospital protocols and policies.

In step 850, the KAM tool 140 identifies and alerts the user to any errors and omissions within the formal expression steps. As noted above, the KAM tool 140 detects any step or stage of the CIG process that is incomplete or improper. Specifically, the KAM tool 140 highlights a portion of the CIG that requires further specifications (e.g., formal expressions) in order to create a complete CIG for a CDS application.

It should be noted that the exemplary method 800 described above is merely an example of any number of steps performable by the KAM tool 140 and related components of the system 100. Accordingly, the KAM tool 140 is not limited to steps recited in exemplary method 800, and may perform additional steps or less steps than steps 805-850. Additional steps may include, for example, receiving modifications to the formal expressions within an existing CIG, merging multiple steps within a CIG based on user modifications, maintaining various clinical guideline properties while modifying a CIG, etc.

Those skilled in the art will understand that the above-described exemplary embodiments may be implemented in any number of manners, including, as a separate software module, as a combination of hardware and software, etc. For example, the KAM tool 140 and related components may be a program containing lines of code stored on a non-transitory computer readable storage medium that, when compiled, may be executed on a processor. It should also be apparent from the above description that the exemplary embodiments allow the processing device to operate more efficiently when executing the KAM tool 140, e.g., by presenting streamlined GUIs, by presenting alerts to direct the user to relevant areas of the guidelines, by creating an opportunity for health care solutions to easily integrate CIG technologies into a vast number of CDS systems and applications, etc.

It is noted that the claims may include reference signs/numerals in accordance with PCT Rule 6.2(b). However, the present claims should not be considered to be limited to the exemplary embodiments corresponding to the reference signs/numerals.

It will be apparent to those skilled in the art that various modifications may be made in the present disclosure, without departing from the spirit or the scope of the disclosure. Thus, it is intended that the present disclosure cover modifications and variations of the invention provided they come within the scope of the appended claims and their equivalents.

What is claimed is:

1. A method, comprising:
prompting a user, via a graphical user interface ("GUI"), for a plurality of clinical guideline entry steps;
receiving, via the GUI, clinical guideline data;
providing, via the GUI, context-sensitive menus;
converting, via the context-sensitive menus, the clinical guideline data into a plurality of formal expression entry steps, wherein only syntactically and semantically correct text entry options are available to the user to build the formal expression entry steps;
receiving, via the GUI, a formal representation of the clinical guideline data;
identifying, via the GUI, at least one step of the formal expression entry steps as being incorrect;
displaying, via the GUI, an alert related to the at least one step identified as incorrect;
prompting the user, via the GUI, for context-specific data related to a clinical decision support ("CDS") system at a clinical site, wherein the GUI displays fields associated with known properties of the CDS system;
receiving, in the displayed fields, the context-specific data related to the CDS system at the clinical site;
mapping the formal representation of the clinical guideline data to a computer interpretable guideline ("CIG") based on a CIG model and the context-specific data related to the CDS system, wherein the CIG provides computer-executable instructions to the CDS system to execute a CDS application in accordance with the clinical guideline data wherein the context-specific data customizes the CIG for a specific location; and
receiving a modification to the CDS application based on a change of one of a protocol or a policy of the specific location wherein the CIG adapts the CDS application based on the change to the one of the protocol or policy.

2. The method of claim 1, further comprising:
identifying at least one step of the plurality of formal expression entry steps as being incomplete; and
displaying an alert related to the at least one step identified as incomplete.

3. The method of claim 1, further comprising:
receiving a modification to an existing CIG; and
adjusting the existing CIG to accommodate the modification.

4. The method of claim 3, wherein the adjusting the existing CIG includes:
merging at least two steps within the plurality of formal expression entry steps; and
maintaining a clinical guideline property within a modified CIG.

5. The method of claim 1, wherein the plurality of formal expression entry steps includes a general content step, an application specific step, and a site specific step.

6. The method of claim 1, further comprising:
receiving and validating log-in credentials of the user;
identifying the user as one of a clinical expert and a knowledge engineer;
adjusting the GUI to one of a clinical view and a formal view based on the identified user; and
sending, via the GUI, a message to a collaborating user for collaborative formulation of the CIG;
wherein the GUI displays an identity of one of the user and the collaborating user as an author of each of the plurality of formal expression entry steps.

7. A system, comprising:
a display for displaying a graphical user interface ("GUI") implemented by a processor, wherein a user sends, by the GUI, a message to a collaborating user for collaborative formulation of a computer interpretable guideline ("CIG"); and
the processor configured to perform operations, comprising:
prompting a user via the GUI for a plurality of clinical guideline entry steps,
receiving clinical guideline data,
providing, via the GUI, context-sensitive menus,
converting, via the context-sensitive menus, the clinical guideline data into a respective plurality of formal expression entry steps, wherein only syntactically and semantically correct text entry options are available to the user to build the formal expression entry steps,
receiving a formal representation of the clinical guideline data,
identifying at least one step of the formal expression entry steps as being incorrect,
displaying an alert related to the at least one step identified as incorrect,
prompting the user, via the GUI, for context-specific data related to a clinical decision support ("CDS") system at a clinical site, wherein the GUI displays fields associated with known properties of the CDS system;
receiving, in the displayed fields, the context-specific data related to the CDS system at the clinical site;
mapping the formal representation of the clinical guideline data to a CIG based on a CIG model and the context-specific data related to the CDS system, wherein the CIG provides computer-executable instructions to the CDS system to execute a CDS application in accordance with the clinical guideline data, wherein the context-specific data customizes the CIG for a specific location; and
receiving a modification to the CDS application based on a change of one of a protocol or a policy of the specific location wherein the CIG adapts the CDS application based on the change to the one of the protocol or policy.

8. The system of claim 7, wherein the processor is further configured to perform operations, comprising:
identifying at least one step of the plurality of formal expression entry steps as being incomplete; and
displaying, via the GUI, an alert related to the at least one step identified as incomplete.

9. The system of claim 7, wherein the processor is further configured to perform operations, comprising:
receiving a modification to the first CIG; and
adjusting the first CIG to accommodate the modification.

10. The system of claim 9, wherein the adjusting the first CIG includes:
merging at least two steps within the plurality of formal expression entry steps; and
maintaining a clinical guideline property within a modified CIG.

11. The system of claim 7, wherein the plurality of formal expression entry steps includes a general content step, an application specific step, and a site specific step.

12. A non-transitory computer readable storage medium including a set of instructions that are executable by a processor, the set of instructions being operable at least to:
prompt a user, via a graphical user interface ("GUI"), for a plurality of clinical guideline entry steps;
receive, via the GUI, clinical guideline data from a user;
provide, via the GUI, context-sensitive menus;
converting, via the context-sensitive menus, the clinical guideline data into a plurality of formal expression entry steps, wherein only syntactically and semantically correct text entry options are available to the user to build the formal expression entry steps;
receive, via the GUI, a formal representation of the clinical guideline data;
identify at least one step of the formal expression entry steps as being incorrect;
display an alert related to the at least one step identified as incorrect;
prompt the user, via the GUI, for context-specific data related to a clinical decision support ("CDS") system at a clinical site, wherein the GUI displays fields associated with known properties of the CDS system;
receive, in the displayed fields, the context-specific data related to the CDS system at the clinical site; and
map the formal representation of the clinical guideline data to a computer interpretable guideline ("CIG") based on a CIG model and the context-specific data related to the CDS system, wherein the CIG provides computer-executable instructions to the CDS system to execute a CDS application in accordance with the clinical guideline data wherein the context-specific data customizes the CIG for a specific location; and
receive a modification to the CDS application based on a change of one of a protocol or a policy of the specific location wherein the CIG adapts the CDS application based on the change to the one of the protocol or policy.

13. The non-transitory computer readable storage medium of claim 12, wherein the set of instructions are further operable to:
identify at least one step of the plurality of formal expression entry steps as being incomplete; and
display an alert related to the at least one step identified as incomplete.

* * * * *